(12) United States Patent
Shaw

(10) Patent No.: US 8,047,840 B2
(45) Date of Patent: Nov. 1, 2011

(54) SHOWER HEAD ATTACHMENT FOR MIXING LIQUIDS USED TO CLEAN TEETH

(75) Inventor: Daniel A Shaw, Naples, FL (US)

(73) Assignee: Health and Hygiene, Inc., Naples, FL (US)

( * ) Notice: Subject to any disclaimer, the term of this patent is extended or adjusted under 35 U.S.C. 154(b) by 0 days.

(21) Appl. No.: 12/586,441

(22) Filed: Sep. 22, 2009

(65) Prior Publication Data

US 2010/0015566 A1    Jan. 21, 2010

Related U.S. Application Data

(63) Continuation-in-part of application No. 11/900,763, filed on Oct. 15, 2007, now abandoned.

(51) Int. Cl.
*A61H 9/00* (2006.01)
(52) U.S. Cl. .......................................... 433/80; 601/162
(58) Field of Classification Search .................... 433/80, 433/82, 83, 89; 601/154, 155, 160, 162, 601/163, 165, 169
See application file for complete search history.

(56) References Cited

U.S. PATENT DOCUMENTS

| 3,225,759 | A | * | 12/1965 | Drapen et al. | 601/165 |
| 3,500,824 | A | * | 3/1970 | Gilbert | 601/165 |
| 4,617,918 | A | * | 10/1986 | Donohue et al. | 601/162 |
| 4,824,368 | A | * | 4/1989 | Hickman | 433/80 |
| 4,941,459 | A | * | 7/1990 | Mathur | 601/165 |
| 5,027,798 | A | * | 7/1991 | Primiano | 601/165 |
| 5,218,956 | A | * | 6/1993 | Handler et al. | 601/155 |
| 5,220,914 | A | * | 6/1993 | Thompson | 601/155 |
| 5,277,582 | A | * | 1/1994 | Jousson | 433/80 |
| 5,484,281 | A | * | 1/1996 | Renow et al. | 433/80 |
| 5,564,629 | A | * | 10/1996 | Weissman et al. | 239/8 |
| 5,626,472 | A | * | 5/1997 | Pennetta | 433/80 |
| 5,685,851 | A | * | 11/1997 | Murphy et al. | 604/150 |
| 7,314,456 | B2 | * | 1/2008 | Shaw | 601/165 |

* cited by examiner

*Primary Examiner* — Ralph A Lewis
(74) *Attorney, Agent, or Firm* — Allen D. Brufsky

(57) ABSTRACT

A valve for adjusting the flow of water through an oral irrigation device is connected to a shower head by a flexible conduit. The valve is located on a handle connected to a water-dispensing pick for cleaning teeth and gums. Mixing apparatus is provided for injecting a secondary fluid, such as a mouthwash, into the flexible conduit upstream from the pick in a direct stream from the shower head.

2 Claims, 4 Drawing Sheets

SHOWER HEAD ATTACHMENT FOR MIXING LIQUIDS USED TO CLEAN TEETH

CROSS-REFERENCES TO RELATED APPLICATIONS

This application is a continuation-in-part application of U.S. application Ser. No. 11/900,763 filed Oct. 15, 2007 now abandoned.

BACKGROUND OF THE INVENTION

1. Field of the Invention

This invention relates to a dental hygiene device, and more particularly to a syringe for delivering a stream of water for cleaning the teeth and gums of a user while showering in combination with an accessory designed to deliver a mixture of the water and another liquid such as a mouthwash dispensed into the water stream.

2. Description of Prior Art

Numerous methods and apparatus have been suggested for cleaning the teeth and gums by using a jet stream of water.

One widely accepted system involves the use of a pulsating jet of water fed to a hand held syringe by an electrically driven pump placed beside a bathroom sink. This system requires a relatively expensive electrically driven pumping mechanism and the use of space adjacent the sink or water basin.

Therefore, it has been suggested that it would be less time consuming and less expensive to clean one's teeth and gums with a stream of water in a shower stall rather than over a sink. Different forms of apparatus designed to utilize an oral syringe in a shower are illustrated in U.S. Pat. Nos. 4,043,337; 4,265,229; 4,564,005; and 4,793,331. However, each of these systems requires a valve at the shower head to divert and redirect the stream of water through the syringe. For disabled persons in a wheelchair or for short people this is a distinct disadvantage negating their use of the device because they cannot reach the valve. Further, diverting the stream at the shower head requires some sort of pressure-lowering mechanism, so the full stream is diverted from the shower head to the cleaning unit and the shower flow is stopped. So the full stream can be used for teeth or gum cleaning. Nor are these devices readily subject to disassembly to replace worn or inoperable parts. In my copending application Ser. No. 11/238,614, filed Sep. 29, 2005, assigned to the same assignee as this application, I disclose a shower head attachment which overcomes the deficiencies of the prior art.

In my copending patent application, the disclosure of which is incorporated herein by reference, a valve for adjusting the flow of water through the device is located on the handle connected to the water-dispensing pick. Rotation of the valve controls the amount and pressure of water dispensed through the pick in a direct stream from the shower head. The valve and its components are threadedly connected between the pick and handle of the device and can be readily disassembled to replace any worn parts.

Furthermore, many users find it desireable to mix a quantity of another liquid with the water stream, such as a mouthwash, to multi-task the cleaning operation. This invention discloses such a mixing apparatus which can be used with the water dispensing pick.

SUMMARY OF THE INVENTION

In accordance with the invention, a container of a secondary liquid source, such as a mouthwash, is joined by two check valves provided within a fitting, and a liquid pump, to inject a quantity of the secondary liquid into the water stream upstream of the pick. One of the check valves closes the secondary liquid source, or mouth of a container, upon a predetermined pressure applied to the liquid pump, such as a syringe, enabling the water from the shower head to mix with a predetermined quantity of the secondary liquid previously dispensed into the fitting body from the secondary liquid source, or container. The syringe pumps the secondary liquid from the fitting body through the second check valve, which closes, to preclude "backwashing" of the mixed liquid from the shower head. The piston of the syringe when pushed forward injects the mixture into the water stream from the shower head. Withdrawal of the syringe piston into its cylinder opens the mouth of the container, or secondary liquid source, so a prescribed quantity of the secondary liquid is dispensed into the fitting and then the piston of the syringe is pushed forward to repeat the process.

BRIEF DESCRIPTION OF THE DRAWING

Further objects and advantages of the invention will become more apparent from the following description and claims and from the accompanying drawing, wherein:

DETAILED DESCRIPTION OF THE PREFERRED EMBODIMENT

Referring my copending application, a shower stall is illustrated which includes a conventional shower head, which receives water under pressure from inlet pipe. An oral irrigating assembly in accordance with the present invention is interposed between shower head and inlet pipe.

The assembly includes a fixture threadedly connected to inlet pipe at one end and the shower head at its opposite end. A flexible conduit is fixed at one end to the fixture which has an opening in communication with the interior of fixture. The distal end of the flexible conduit is received within the interior of a handle component and connected over the serrated end of a housing.

The housing threadedly receives a valve having a threaded cylindrical portion, received in threaded engagement with a complementary threaded portion within the housing. Rotation of threaded portion by means of a handle moves the valve element linearly, relatively out of housing, while rotation in an opposite direction moves the valve linearly into the housing.

At the end of valve is a nipple which seats within the bore of the housing and blocks then the ingress of water from the conduit through the handle component. Rotation of the handle to open the valve, by moving it out of the housing, moves the nipple out of the bore. This enables water to enter the housing, flow around the nipple past an O-ring seal and against an O-ring seal on the valve and through an opening into the interior of the housing. Depending on the distance of travel of the valve relative to the housing, the pressure and amount of the water delivered through opening can be varied. To preclude the ingress of water from conduit through valve, the valve handle is turned in an opposite direction until the O-ring seal seats on a housing valve seat, effectively shutting the valve and precluding the ingress of water through the housing.

Connected to the valve by a pair of oppositely extending projections received in the openings on the valve is a water pick having an elongated nozzle, provided with an opening. Water streaming through the valve emanating from the shower head is conducted through the interior of nozzle against the teeth and/or gums of a user to clean the same.

Figure 1:
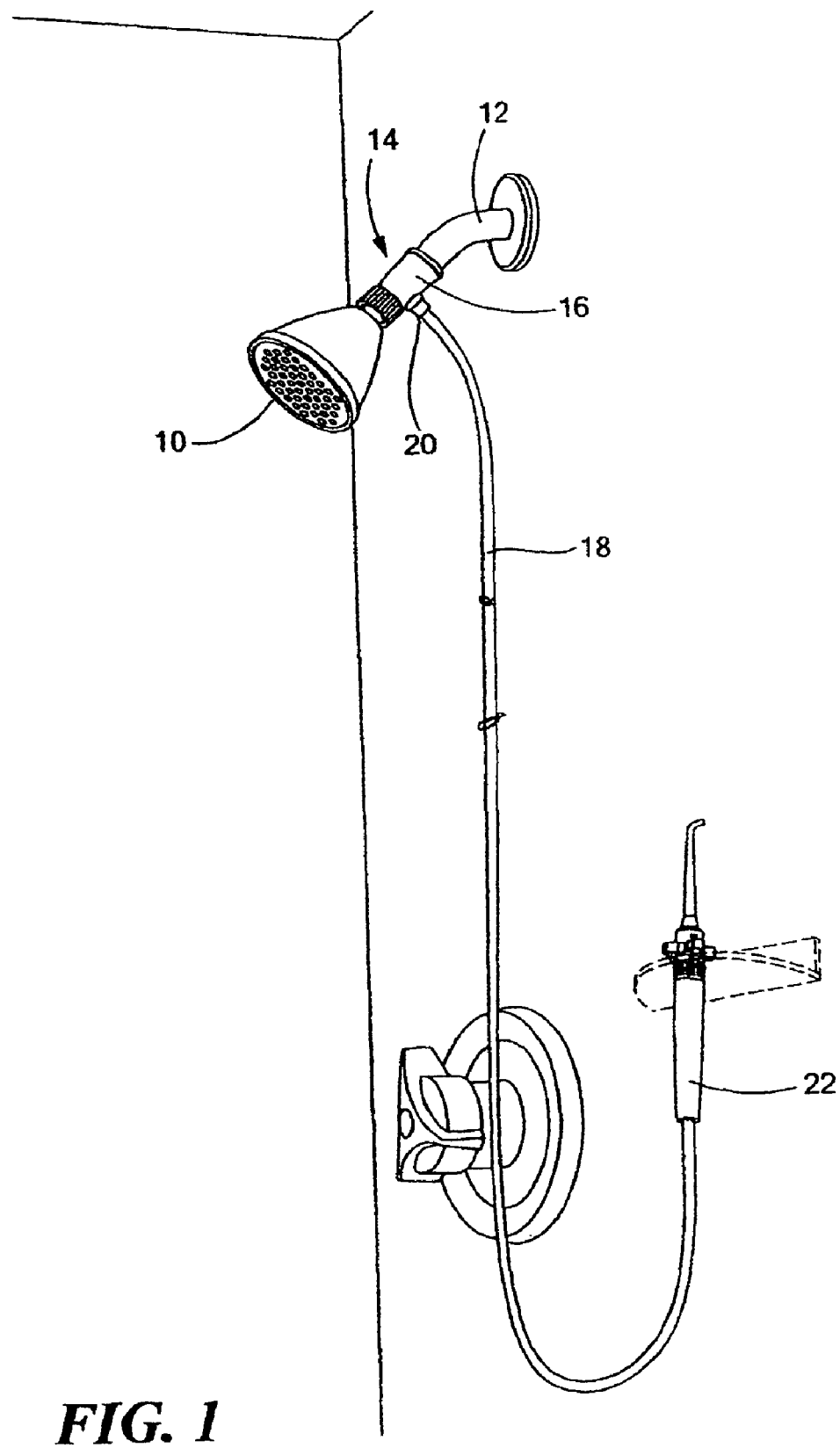
FIG. 1 is a fragmentary perspective view of a shower head attachment to which the mixing apparatus of the present invention can be attached.
Figure 2:
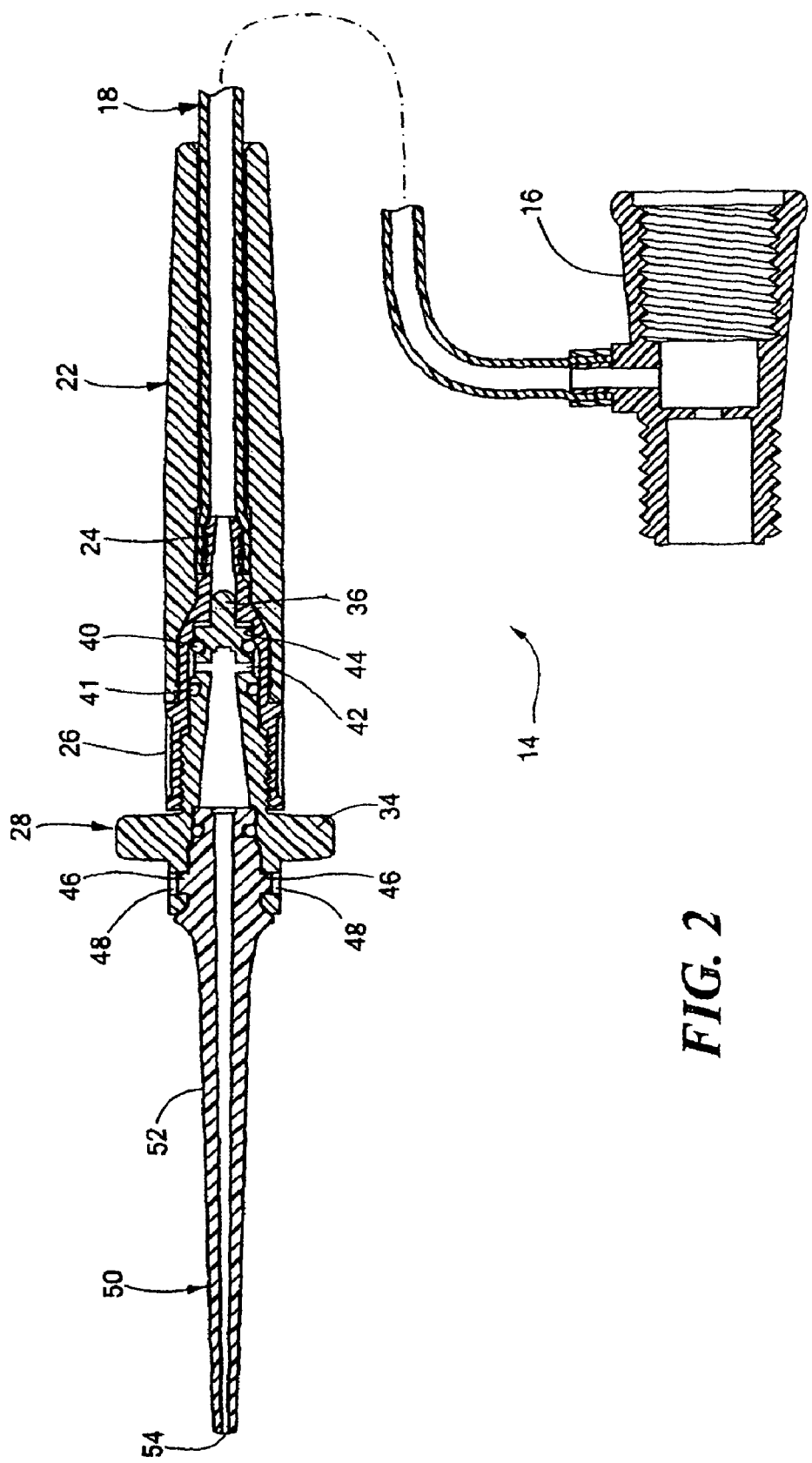
FIG. 2 is a longitudinal cross-sectional view of the shower head attachment of FIG. 1.
Figure 3:
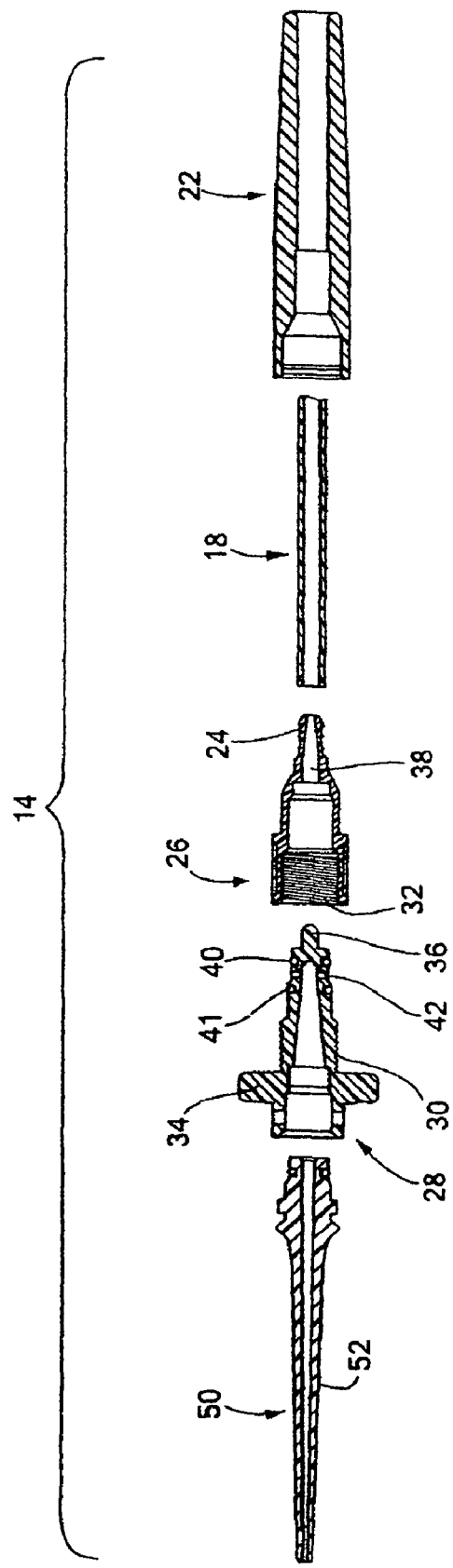
FIG. 3 is an exploded cross-sectional view of the components of the shower head attachment of FIG. 2.
Figure 4:
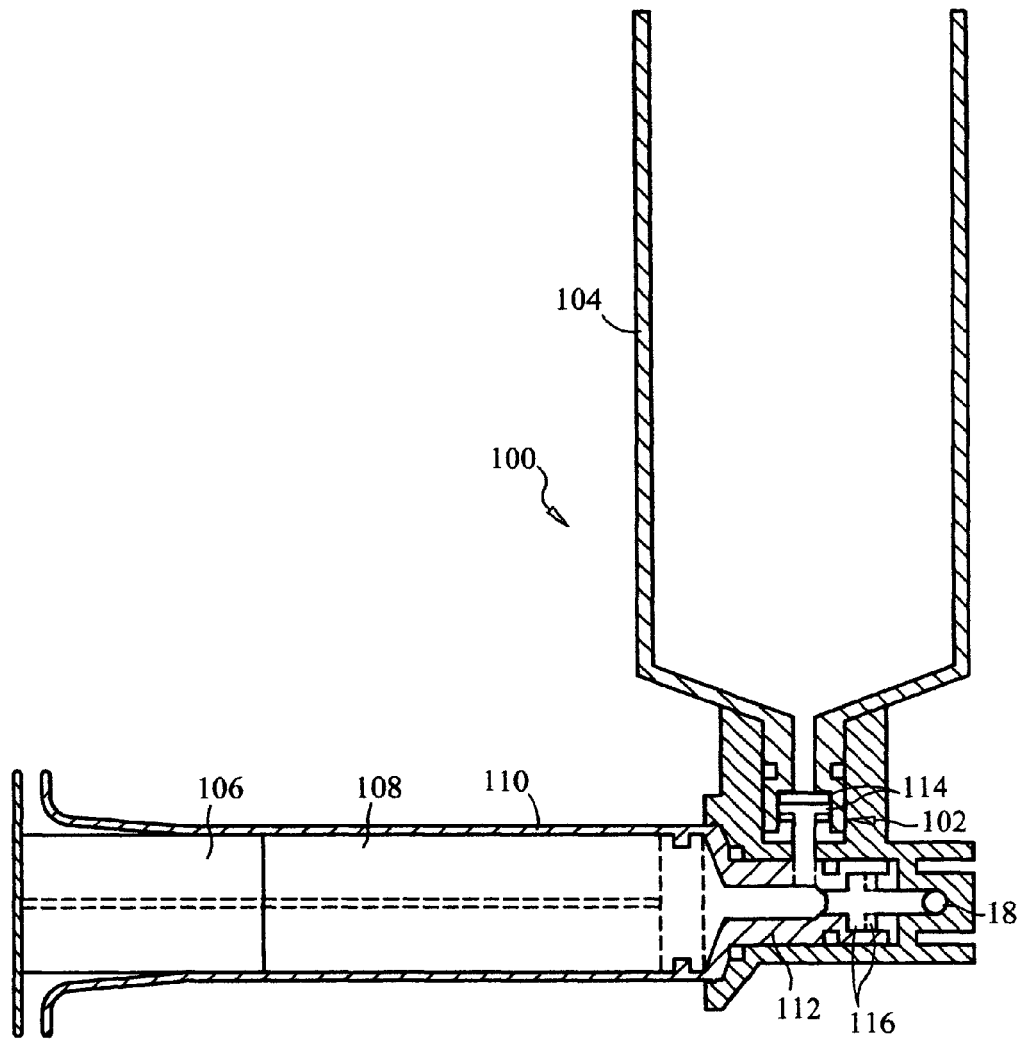
FIG. 4 is a diagrammatic cross-sectional view of the components of the mixing apparatus of the present invention.

Referring now to FIG. 4 of this application, the apparatus 100 of the present invention is provided with a fitting receiving a container 104 for receiving a quantity of a secondary liquid, such as a mouthwash, to be mixed with the water diverted from the shower head. The mixing apparatus includes a syringe 106 having a hand-operable, linearly moving, plunger or piston 108 in an outer cylinder 110. The fitting 102 receives a portion of the flexible conduit 18 of the shower attachment upstream of the pick assembly. The flexible conduit 18 is opened in a sidewall thereof to provide fluid communication with a chamber 112 in fitting 102.

The container 104 filled with a secondary liquid such as a mouthwash, is joined by two check valves 114, 116 provided within the chamber 112 of fitting 102 to the opened sidewall of flexible conduit 18. A liquid pump, such as syringe 106, is used to inject a quantity of the secondary liquid into the water stream flowing through conduit 18 upstream of the pick.

One of the check valves 114 closes the mouth of secondary liquid source container 104, upon a predetermined pressure applied to the piston 108 of the liquid pump syringe, as shown in the full line position of check valve 114, while enabling the water from the shower head to mix with a predetermined quantity of the secondary liquid previously dispensed into the fitting chamber 112 from the secondary liquid source container 104. The syringe piston 108 pumps the secondary liquid from the fitting body chamber 116 through the second check valve 116, which opens to the dotted line position and which closes to its full line position indicated in FIG. 4, to preclude "backwashing" of the mixed liquid from the shower head upon withdrawal of the piston 108 in cylinder 110. The piston 108 of the syringe when pushed forward injects the liquid in chamber 112 into the water stream into the conduit 18 between the pick and the shower head. Withdrawal of the syringe piston 108 into its cylinder 110 opens the mouth of the container 104, as the withdrawal relieves the pressure on the check valve 114 so it can open by dropping to its dotted line position as indicated in FIG. 4, so a prescribed quantity of the secondary liquid is dispensed into the fitting chamber 112 and then the piston 106 of the syringe is pushed forward to repeat the process by injecting the secondary liquid into conduit 18 and opening check valve 116 while closing check valve 114.

What is claimed as new is:

1. Dental cleaning apparatus in combination with a water outlet and a showerhead, said apparatus comprising:
    a fixture between said water outlet and showerhead for diverting water from said water outlet,
    a flexible conduit in fluid communication with said fixture to receive diverted water from said water outlet,
    a handle element communicating with an opposite end of said flexible conduit to receive the diverted water,
    a valve body provided with a handle portion received within said handle element including
    means for precluding communication of said handle element with said flexible conduit upon movement in one direction, but enabling communication upon movement in an opposite direction,
    an oral irrigator coupled to said valve body for transmitting a jet of water to a user of the apparatus upon movement of said valve body enabling communication between said handle element and flexible conduit, and
    a mixing apparatus adapted to be placed in fluid communication with said flexible conduit for injecting a secondary liquid into said diverted water,
    said mixing apparatus including
    a container having an opening for dispensing a secondary fluid housed within said container, and
    a fluid pump for moving said secondary fluid dispensed through said container opening into said flexible conduit,
    a fitting having a fluid chamber receiving said container, said fluid pump and said flexible conduit being in fluid communication,
    a first check valve disposed in said fitting between said container and chamber,
    a second check valve disposed between said fluid pump in said chamber and said flexible conduit,
    whereupon pressure imparted to any fluid in said chamber will close the first check valve and communication between said fitting chamber and container, while opening the second check valve between said fitting chamber and flexible conduit enabling fluid in said chamber to be injected into said flexible conduit,
    said fluid pump including
    means for relieving the pressure in said chamber to open said first check valve and close said second check valve so an amount of said secondary fluid can be dispensed from said container into said fitting chamber.

2. Dental cleaning apparatus in combination with a water outlet and a showerhead, said apparatus comprising:
    a fixture between said water outlet and showerhead for diverting water from said water outlet,
    a flexible conduit in fluid communication with said fixture to receive diverted water from said water outlet,
    a handle element communicating with an opposite end said flexible conduit to receive the diverted water,
    a valve body provided with a handle portion received within said handle element including
    means for precluding communication of said handle element with said flexible conduit, said means for precluding communication of said handle element with said flexible conduit being operational upon movement in one direction, but enabling communication upon movement in an opposite direction,
    an oral irrigator coupled to said valve body for transmitting a jet of water to a user of the apparatus upon movement of said valve body enabling communication between said handle element and flexible conduit, and
    a mixing apparatus adapted to be placed in fluid communication with said flexible conduit for injecting a secondary liquid into said diverted water,
    said mixing apparatus including
    a container having an opening for dispensing a secondary fluid housed within said container,
    a fluid pump for moving said secondary fluid dispensed through said container opening into said flexible conduit, said fluid pump being
    a syringe provided with a linearly slidable, retractable piston in a cylinder,
    a fitting having a fluid chamber receiving said container, piston and said flexible conduit in fluid communication, and
    a first check valve disposed in said fitting between said container and chamber,
    a second check valve disposed between said piston in said chamber and said flexible conduit, whereupon pressure imparted to any fluid in said chamber will close the first check valve and communication between said fitting chamber and container, while opening the second check valve between said fining chamber and flexible conduit enabling fluid in said chamber to be injected into said flexible conduit by said piston, said piston upon withdrawal from said chamber will relieve the pressure in said chamber to open said first check valve and close said second check valve so an amount of said secondary fluid can be dispensed from said container into said fitting chamber.

* * * * *